(12) United States Patent
Uhland et al.

(10) Patent No.: US 10,328,203 B2
(45) Date of Patent: Jun. 25, 2019

(54) SENSOR SYSTEM FOR DRUG DELIVERY DEVICE, DRUG DELIVERY DEVICE HAVING THE SAME AND METHOD OF USING THE SAME

(71) Applicant: PALO ALTO RESEARCH CENTER INCORPORATED, Palo Alto, CA (US)

(72) Inventors: Scott Albert Uhland, San Jose, CA (US); Eric Peeters, Mountain View, CA (US); Bryan Thomas Preas, Battle Ground, OR (US); Joerg Martini, San Francisco, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 372 days.

(21) Appl. No.: 15/298,456

(22) Filed: Oct. 20, 2016

(65) Prior Publication Data
US 2017/0035970 A1    Feb. 9, 2017

Related U.S. Application Data

(63) Continuation of application No. 12/356,824, filed on Jan. 21, 2009, now Pat. No. 9,480,795.

(51) Int. Cl.
*A61M 5/168*    (2006.01)
*A61M 5/172*    (2006.01)

(52) U.S. Cl.
CPC ........ *A61M 5/1723* (2013.01); *A61M 5/1684* (2013.01); *A61M 5/16836* (2013.01); *A61M 2205/3303* (2013.01); *A61M 2205/3306* (2013.01); *A61M 2205/3317* (2013.01); *A61M 2205/3368* (2013.01)

(58) Field of Classification Search
CPC ..................... A61M 5/1723; A61M 55/16836
See application file for complete search history.

(56) References Cited

U.S. PATENT DOCUMENTS

| 4,647,281 A | 3/1987 | Carr |
| 5,697,899 A | 12/1997 | Hillman et al. |
| 6,491,666 B1 | 12/2002 | Santini, Jr. et al. |
| 6,527,762 B1 | 3/2003 | Santini, Jr. et al. |

(Continued)

FOREIGN PATENT DOCUMENTS

| EP | 1342482 | 9/2003 |

OTHER PUBLICATIONS

Partial EP Search Report dated Jun. 15, 2010, corresponding to European Application N. 10151234.1.

*Primary Examiner* — Nathan R Price
*Assistant Examiner* — Melissa A Snyder
(74) *Attorney, Agent, or Firm* — Miller Nash Graham & Dunn LLP

(57) ABSTRACT

A system for use with a drug delivery device includes a sensor unit and a deactivation unit operatively coupled to an output of the sensor unit and to a drug-retaining region of the drug delivery device, wherein the drug-retaining region contains a drug. The sensor unit is configured to detect a characteristic of a local environment and generate an output corresponding to a value of the detected characteristic. The deactivation unit is configured to render the drug ineffective when the output of the sensor unit satisfies a predetermined condition.

23 Claims, 5 Drawing Sheets

(56) References Cited

U.S. PATENT DOCUMENTS

| | | |
|---|---|---|
| 6,537,256 B2 | 3/2003 | Santini, Jr. et al. |
| 6,669,683 B2 | 12/2003 | Santini, Jr. et al. |
| 6,730,072 B2 | 5/2004 | Shawgo et al. |
| 6,807,965 B1 | 10/2004 | Hickle |
| 6,827,250 B2 | 12/2004 | Uhland et al. |
| 6,875,208 B2 | 4/2005 | Santini, Jr. et al. |
| 7,041,130 B2 | 5/2006 | Santini, Jr. et al. |
| 7,052,488 B2 | 5/2006 | Uhland |
| 7,070,592 B2 | 7/2006 | Santini, Jr. et al. |
| 7,114,312 B2 | 10/2006 | Coppeta et al. |
| 7,410,616 B2 | 8/2008 | Santini, Jr. et al. |
| 7,413,846 B2 | 8/2008 | Maloney et al. |
| 9,480,795 B2 * | 11/2016 | Uhland ............. A61M 5/16836 |
| 2002/0151776 A1 | 10/2002 | Shawgo et al. |
| 2002/0173745 A1 | 11/2002 | Santini, Jr. et al. |
| 2002/0183721 A1 | 12/2002 | Santini, Jr. et al. |
| 2003/0010808 A1 | 1/2003 | Uhland et al. |
| 2003/0105455 A1 | 6/2003 | Santini, Jr. et al. |
| 2004/0034332 A1 | 2/2004 | Uhland |
| 2004/0143236 A1 | 7/2004 | Santini, Jr. et al. |
| 2004/0247671 A1 | 12/2004 | Prescott et al. |
| 2005/0050859 A1 | 3/2005 | Coppeta et al. |
| 2005/0077584 A1 | 4/2005 | Uhland et al. |
| 2005/0215991 A1 | 9/2005 | Altman et al. |
| 2006/0024358 A1 | 2/2006 | Santini, Jr. et al. |
| 2006/0057737 A1 | 3/2006 | Santini, Jr. et al. |
| 2007/0016163 A1 | 1/2007 | Santini, Jr. et al. |
| 2007/0036835 A1 | 2/2007 | Coppeta et al. |
| 2008/0015494 A1 | 1/2008 | Santini et al. |
| 2008/0033260 A1 | 2/2008 | Sheppard et al. |
| 2008/0076975 A1 | 3/2008 | Santini, Jr. et al. |

\* cited by examiner

SENSOR SYSTEM FOR DRUG DELIVERY DEVICE, DRUG DELIVERY DEVICE HAVING THE SAME AND METHOD OF USING THE SAME

CROSS REFERENCE TO RELATED APPLICATION

This application is a continuation of and claims priority to U.S. patent application Ser. No. 12/356,824 filed on Jan. 21, 2009, which is incorporated here by reference in its entirety.

TECHNICAL FIELD

Embodiments exemplarily described herein are generally related to sensor systems for drug delivery devices and, more particularly, sensor systems configured to facilitate a determination whether a drug within a drug delivery device should be rendered ineffective.

BACKGROUND

Generally, drug delivery devices (such as inhalers, syringes, intravenous bags, implantable drug delivery systems, transdermal patches, pill bottles, liquid medicine bottles, eyedroppers, etc.) store drugs until the drugs are required by a user. There are numerous occasions when it would be desirable to render the drugs contained within such drug delivery devices ineffective either automatically or manually in order to prevent the drug from being improperly released into the public (e.g., though the public water supply, through the garbage, etc.) or improperly obtained (e.g., through tampering of the drug delivery device).

It was the understanding and recognition of these and other problems associated with the conventional art that formed the impetus for the embodiments exemplarily described herein.

DETAILED DESCRIPTION OF THE EMBODIMENTS

Figure 1:
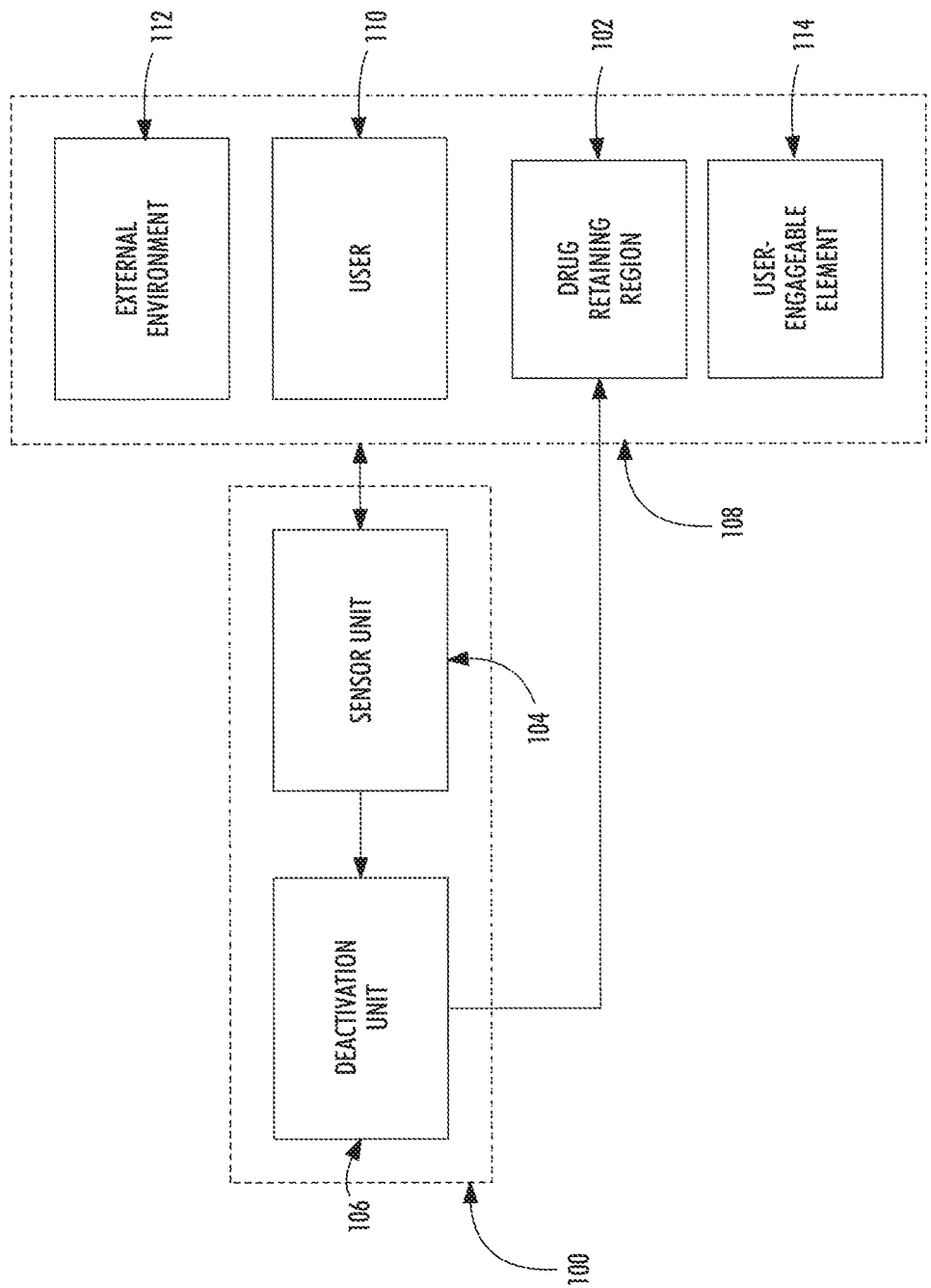
FIG. 1 schematically illustrates elements of a sensor system for use with a drug delivery device.

FIG. 1 schematically illustrates elements of a sensor system for use with a drug delivery device.

Referring to FIG. 1, a sensor system 100 may be provided for use with a drug delivery device (not shown). The drug delivery device may include a drug-retaining region 102 containing a drug. An exemplary discussion of drug delivery devices capable of use with the sensor system 100 is provided with respect to FIG. 2.

As illustrated in FIG. 1, the sensor system 100 may, for example, include a sensor unit 104 and a deactivation unit 106 operatively coupled to an output of the sensor unit 104 and to the drug-retaining region 102 of the drug delivery device. The sensor unit 104 may be configured to detect a characteristic of a local environment 108 and generate an output corresponding to a value of the detected characteristic. The deactivation unit 106 may be configured to render the drug ineffective when the output of the sensor unit 104 satisfies a predetermined condition.

The deactivation unit 106 may be operatively coupled to an output of the sensor unit 104 via a wired or wireless communication medium.

The characteristic of the local environment 108 detectable by the sensor unit 104 include a mechanical characteristic, a thermal characteristic, an electrical characteristic, an optical characteristic, a chemical characteristic, or the like or a combination thereof.

The local environment 108 may include the drug-retaining region 102, the user 110, a region outside the user 110 and the drug delivery device (hereinafter referred to as an "external environment 112"), a user-engageable element 114 or the like or a combination thereof. A characteristic of the user-engageable element 114 is detectable by the sensor unit 104 when the user engages with the user-engageable element 114.

As used herein, the term "drug" refers to any material intended for use in the diagnosis, cure, mitigation, treatment, or prevention of disease in a human or other animal, or any material (other than food) which affects the structure or any function of the body of a human or other animal. Thus, a drug is rendered "ineffective" when its intended use is prevented from being realized by the user. For example, a drug's intended use is prevented from being realized by the user when the drug cannot be cannot be transported from the drug-retaining region 102 to a location outside the drug delivery device, when the drug is neutralized within the drug-retaining region 102, when the bio-activity of the drug is blocked within the user, or the like or a combination thereof.

In one embodiment, the predetermined condition is satisfied when the value of a detected characteristic of the local environment 108 is outside a predetermined range for the detected characteristic, when the value of a detected characteristic of the local environment 108 is outside a predetermined range for the detected characteristic, when a rate at which the value of a detected characteristic of the local environment 108 changes is outside a predetermined range for the detected characteristic, or the like or a combination thereof.

Figure 2:
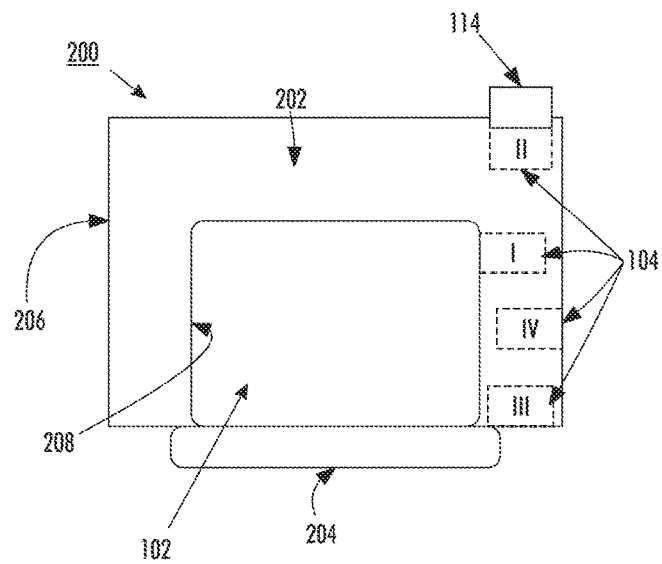
FIG. 2 schematically illustrates a drug delivery device usable with the sensor system shown in FIG. 1, in accordance with some embodiments.

FIG. 2 schematically illustrates a drug delivery device usable with the sensor system shown in FIG. 1.

Referring to FIG. 2, a drug delivery device 200 capable of use with the sensor system 100 may, for example, include a housing 202, within which the aforementioned drug-retaining region 102 is located, and a barrier 204 coupled to the housing 202.

Generally, the housing 202 is configured to maintain the effectiveness of drug within the drug-retaining region 102 within a predetermined environment. In one embodiment, the predetermined environment may be air having a controlled room temperature (e.g., about 68° C. to about 77° F.). In another embodiment, the predetermined environment may be within the user's body.

The housing 202 may be formed from a single, integral structure or may be formed from a plurality of separate structures. The housing 202 may have an exterior surface 206, which is exposed to an external environment, and an interior surface 208, which is exposed to a drug contained within the drug-retaining region 102. The exterior surface 206 and the interior surface 208 of the housing 202 may be formed of the same material or be formed from different materials. In one embodiment, at least a portion of the housing 202 may be substantially rigid so as to retain a predetermined shape during transportation, use and/or storage of the drug delivery device 200. In another embodiment, at least a portion of the housing 202 may be elastically deformable so as to change the volume of the drug-retaining region 102 in a manner that facilitates (e.g., induces or aids) transportation drug within the drug-retaining region 102 to a location outside the drug delivery device 200. In another embodiment, at least a portion of the housing 202 may be plastically deformable so as to facilitate transportation drug within the drug-retaining region 102 to a location outside the drug delivery device 200.

The barrier 204 communicates with the interior of the drug-retaining region 102 and the location outside the drug delivery device 200. Thus, according to some embodiments, the barrier 204 defines at least a portion of the drug-retaining region 102, the barrier 204 contacts at least a portion of the drug-retaining region 102, the barrier 204 is exposed to drug within the drug-retaining region 102, or a combination thereof. The barrier 204 may be formed from a single, integral structure or may be formed from a plurality of separate structures. The barrier 204 and the housing 202 may be formed from a single, integral structure or may be formed from a plurality of separate structures. The barrier 204 and the housing 202 may be formed of the same material or from different materials. In one embodiment, barrier 204 may comprise a solid, a liquid, a gel, a gas or a combination thereof. As exemplarily shown in FIG. 2, the barrier 204 is coupled to the exterior surface 206 of the housing 202. In another embodiment, however, the barrier 204 may be embedded within the housing 202.

In one embodiment, the drug is transported from the drug-retaining region 102 to a location outside the drug delivery device 200 when the barrier 204 is partially or completely removed the barrier 204 from the housing 202. In such an embodiment, the barrier 204 may, for example, be hingedly coupled to the housing 202. In another example, the barrier 204 and the housing 202 may include complementary screw-type threads such that the barrier 204 may be screwed to the housing 202. In yet another example, the barrier 204 and the housing 202 may include structures configured in any known manner suitable to provide selective coupling and decoupling of the barrier 204 and housing 202.

In another embodiment, the drug is transported from the drug-retaining region 102 to a location outside the drug delivery device 200 when the drug delivery device 200 is accomplished by deforming the barrier 204. In such an embodiment, the barrier 204 may, for example, be rupturable so as to allow drug within the drug-retaining region 102 to pass therethrough.

In another embodiment, the drug is transported from the drug-retaining region 102 to a location outside the drug delivery device 200 when a pressure within the drug-retaining region 102 is increased. In such an embodiment, the barrier 204 may, for example, be provided as a capillary passage through which drug within the drug-retaining region 102 can be travel when pressure within the drug-retaining region 102 exceeds a threshold amount.

In another embodiment, the drug is transported from the drug-retaining region 102 to a location outside the drug delivery device 200 when drug diffuses through the barrier 204 to, for example, a tissue of the user. As used herein "tissue" refers to any group of cells that performs a biological function (e.g., skin, nails, blood, mucosa, etc.).

As exemplarily illustrated, the user-engageable element 114 is coupled to the housing 202 so as to be directly engageable the user (e.g., exposed at the exterior surface 206 of the housing 202). In another embodiment, however, the user-engageable element 114 may be disposed within the housing 202 or within the drug-retaining region 102. In such an embodiment, at least a portion of the housing 202 may be elastically or plastically deformable so that the user may physically engage with the user-engageable element 114 via the housing 202. In many embodiments, the user-engageable element 114 is configured to be intentionally engaged by the user when, for example, the user no longer requires the drug within the drug-retaining region 102. In one embodiment, however, the user-engageable element 114 is configured to be incidentally engaged when, for example, the drug delivery device is being tampered with (e.g., the housing 202 is being tampered with to remove the drug within the drug-retaining region 102).

Constructed as exemplarily described above, the drug delivery device 200 may be provided as an inhaler, a syringe, an intravenous bag, an implantable drug delivery system, a transdermal patch, a pill bottle, a liquid medicine bottle an eyedropper, or the like or a combination thereof. Thus, the drug within the drug-retaining region 102 of the drug delivery device 200 may be transportable to the user via inhalation, injection, passive transdermal delivery, active transdermal delivery, oral ingestion, in vivo delivery, topical delivery, or the like or a combination thereof.

In one embodiment, the sensor unit 104 may include at least one sensor arranged operably proximate to the drug-retaining region 102 (e.g., at location I), at least one sensor arranged operably proximate to the user-engageable element 114 (e.g., at location II), at least one sensor arranged so as to be operably proximate to the user when the user is within an operable range of the drug delivery device 200 (e.g., at location III), at least one sensor arranged so as to be operably proximate to an external environment outside the drug delivery device 200 and the user (e.g., at location IV), or a combination thereof. An exemplary discussion of sensors of the sensor unit 104 that may be arranged operably proximate to the aforementioned local environments 108 (i.e., the drug-retaining region 102, the user-engageable element 114, the user 110, and the external environment 112) is provided in the paragraphs below.

When the sensor unit 104 includes at least one sensor arranged operably proximate to the drug-retaining region 102 (e.g., at location I), the sensor unit 104 may detect a mechanical characteristic, a thermal characteristic, an electrical characteristic, an optical characteristic, a chemical characteristic, or the like or a combination thereof of the drug-retaining region 102 that is dependent on the amount of drug contained within the drug-retaining region 102 and generate an output corresponding to a value of the detected characteristic. Thus, the value of the detected characteristic may correspond to the amount of drug contained within the drug-retaining region 102. Accordingly, the value of the characteristic detected by the sensor unit 104 may be outside a predetermined range when the amount of drug contained within the drug-retaining region 102 is below a threshold amount. In addition, the rate at which the value detected by the sensor unit may be outside a predetermined range when the rate at which drug is transported out of the drug-retaining region 102 (i.e., the "drug transport rate") exceeds the drug transport rate when the user is within the operable range of the drug delivery device (i.e., a "normal drug transport rate"). Therefore, the predetermined condition may be satisfied when the amount of drug contained within the drug-retaining region 102 is below a threshold amount, when the drug transport rate exceeds a normal drug transport rate, or a combination thereof.

A mechanical characteristic of the drug-retaining region 102 may, for example, include pressure, mass, or the like or a combination thereof, which changes as the amount of drug contained within the drug-retaining region 102 changes. Accordingly, the sensor unit 104 may include at least one sensor such as a pressure sensor, an accelerometer, or the like or a combination thereof. In another example, a mechanical characteristic of the drug-retaining region 102 may include an acoustic wave propagation characteristic within the drug-retaining region 102. Accordingly, the sensor unit 104 may include an acoustic emitter (e.g., a speaker) and an acoustic detector (e.g., a microphone). The acoustic detector may detect a change in the amount or presence of a drug or drug matrix within the drug-retaining region 102 by monitoring a change in propagation velocity of acoustic waves emitted by the acoustic emitter, a phase change of acoustic waves emitted by the acoustic emitter, the transmitted intensity of acoustic waves emitted by the acoustic emitter, a reflected intensity of acoustic waves emitted by the acoustic emitter, a scattered intensity of acoustic waves emitted by the acoustic emitter, an absorbed intensity of acoustic waves emitted by the acoustic emitter, or the like or a combination thereof.

A thermal characteristic of the drug-retaining region 102 may, for example, include temperature, thermal conductivity, thermal resistance, or the like or a combination thereof, which changes as the amount of drug contained within the drug-retaining region 102 changes. Accordingly, the sensor unit 104 may include at least one temperature sensor such as a thermometer, a thermistor, a thermocouple, a temperature sensitive resistor, or the like or a combination thereof.

An electrical characteristic of the drug-retaining region 102 may, for example, include dielectric constant, electrical conductivity, electrical inductance, electrical impedance, electrical resistance, or the like or a combination thereof, which changes as the amount of drug contained within the drug-retaining region 102 changes. Accordingly, the sensor unit 104 may include at least one electrical sensor such as an electrical resistance sensor, an electrical current sensor, an electrical voltage sensor, or the like or a combination thereof.

For example, the ionic conductivity of the drug-retaining region 102 may be highly dependent on the amount of drug retained within the drug-retaining region 102, particularly in the case where the drug has a net non-zero charge. Accordingly, the sensor unit 104 may include two electrodes configured to measure DC impedance therebetween two electrodes can provide characteristic resistances or, inversely, conductivity. Ionic conductivity of the drug-retaining region 102 is directly dependent on the charged drug content. In another example, the sensor unit 104 may include a reference standard electrode to perform impedance spectroscopy, thereby offering the ability to monitor a resonant frequency characteristic of the drug, as well as phase and intensity shifts resulting from changes in the drug concentration or electrode configuration.

An optical characteristic of the drug-retaining region 102 may, for example, include optical transmittance, index of refraction, optical reflectance, or the like or a combination thereof, which changes as the amount of drug contained within the drug-retaining region 102 changes. Accordingly, the sensor unit 104 may include at least one optical sensor such as a photodetector (e.g., sensitive to visible light, infra-red light, ultraviolet light, or the like) configured to detect an optical characteristic of the drug-retaining region 102. In one example, the sensor unit 104 may further include a light-emitting element (e.g., an LED) configured to transmit light (e.g., visible light, infra-red light, ultraviolet light or the like) through the drug-retaining region 102 to the photodetector.

In one embodiment, the optical characteristic of the drug-retaining region 102 includes the interaction of light with the drug or with a light-conducting medium within which the drug is retained. In the case where the drug is an integral part of the light-conducting medium, the drug may have a characteristic absorption band. Accordingly, the sensor unit 104 may include one or more LEDs and/or photodiodes configured to monitor the characteristic absorption band of the drug. The drug may act as a scattering center (immiscible mass or particulate). The rate of drug usage can be tracked by monitoring the reduction in the scattered light signal. In another embodiment, the removal of the drug from the light-conducting medium may produce voids or fluctuations in the index of refraction yielding an increase in the scattered light signal.

In another embodiment, the optical characteristic of the drug-retaining region 102 includes the potential fluorescence characteristics of the drug. Upon illumination at the appropriate wavelength, the drug may fluoresce. This fluorescence can be monitored for intensity shifts resulting from drug usage. Accordingly, the sensor unit 104 may include one or more LEDs and/or photodiodes configured to cause the drug to fluoresce.

In another embodiment, the optical characteristic of the drug-retaining region 102 includes a supplemental optical signature corresponding, for example, to the expiration of the drug. In this case, the drug-retaining region 102 may further retain a marker (e.g., a dye) that changes color over time. The color change could result from time lapse, pH change or moisture exposure. Again using a simple broad band light source, a filter and a photodiode, the designed end of use could be digitally detected by the sensor unit 104.

A chemical characteristic of the drug-retaining region 102 may, for example, include the chemical composition of a material adjacent to a sensor at a location within/adjacent to the drug-retaining region 102, or the like, that changes as the amount of drug contained within the drug-retaining region 102 changes. Accordingly, the sensor unit 104 may include at least one chemical sensor such as a gas sensor (e.g., sensitive to air, carbon dioxide, carbon monoxide, oxygen, methane, or the like, or a combination thereof), a liquid sensor (e.g., sensitive to water, drug compositions, or the like, or a combination thereof), or the like or a combination thereof.

In one embodiment, a chemical characteristic of the drug-retaining region 102 may include pH. Accordingly, the sensor unit 104 may be provided as a pH sensor. In one embodiment, pH may increase or decrease upon a decrease in drug concentration. Commercially available Ag/AgCl miniaturized pH electrodes may be used to locally monitor the proton concentration of the drug-retaining region 102. In another embodiment, the sensor unit 104 may include ion-selective membranes integrated with a pH sensor, thereby providing pathways to measure ions such as potassium, calcium, sodium, etc., which allows for the direct or indirect measurement of the drug concentration. More complex drug delivery systems (e.g., IV delivery devices used within a hospital setting) may use miniaturized field asymmetric waveform ion mobility spectrometry to monitor the head space in the drug-retaining region 102. The vapors present in the drug-retaining region 102 may be directly correlated to the remaining concentration and the rate of consumption.

When the sensor unit 104 includes at least one sensor arranged operably proximate to the user-engageable element 114 (e.g., at location II), the sensor unit 104 may detect a mechanical characteristic, a thermal characteristic, an electrical characteristic, an optical characteristic, a chemical characteristic, or the like or a combination thereof of the user-engageable element 114 that is present when the user engages with the user-engageable element 114 and generate an output corresponding to a value of the detected characteristic. Accordingly, the value of the characteristic detected by the sensor unit 104 may be within a predetermined range when the user-engages with the user-engageable element 114. Therefore, the predetermined condition may be satisfied when the user engages with the user-engageable element 114.

A mechanical characteristic of the user-engageable element 114 may, for example, include pressure, mass, or the like or a combination thereof, which changes when the user engages with the user-engageable element 114. Accordingly, the sensor unit 104 may include at least one sensor such as a pressure sensor, an accelerometer, or the like or a combination thereof.

In one embodiment, the user-engageable element 114 may be provided as a mechanical switch. Activation of the switch by the user may generate an electrical signal indicating that a predetermined condition has occurred. The switch may, for example, include a single-use push-to-connect button. When the drug delivery device 200 is provided as a transdermal patch, the user-engageable element 114 may be mechanically activated during the process of removing the patch from the user's skin. Such a user-engageable element 114 may be provided as a switch or a stress/strain gauge.

In another embodiment, the user-engageable element 114 may be provided as a piezoelectric element. The piezoelectric element may be mechanically deformed when the user engages with the user-engageable element 114. Upon being mechanically deformed, an electric current may be generated by the piezoelectric element as the output of the sensor unit 104. In one embodiment, the piezoelectric element may be directly engageable by the user when the user engages with the user-engageable element 114. In another embodiment, the piezoelectric element may be indirectly engageable by the user. In such an embodiment, the user-engageable element 114 may include an intermediate element that can be actuated by the user when the user engages with the user-engageable element 114. Upon being actuated, the intermediate element contacts the piezoelectric element. Therefore, the piezoelectric element may be indirectly engageable by the user when the user engages with the user-engageable element 114.

A thermal characteristic of the user-engageable element 114 may, for example, include temperature, thermal conductivity, thermal resistance, or the like or a combination thereof, which changes when the user engages with the user-engageable element 114. Accordingly, the sensor unit 104 may include at least one temperature sensor such as a thermometer, a thermocouple, a thermistor, a temperature sensitive resistor, or the like or a combination thereof.

In one embodiment, the user-engageable element 114 may include an element that is thermally coupled to the sensor unit 104. The user may engage with the user-engageable element 114 (e.g., by placing a finger onto the user-engageable element 114) to locally heat the element above a predetermined threshold temperature. The element may also be heated above the threshold temperature using standard household appliances (e.g., hair dryer, microwave oven, or the like).

An electrical characteristic of the user-engageable element 114 may, for example, include dielectric constant, electrical conductivity, electrical inductance, electrical impedance, electrical resistance, or the like or a combination thereof, which changes when the user engages with the user-engageable element 114. Accordingly, the sensor unit 104 may include at least one electrical sensor such as an electrical resistance sensor, an electrical current sensor, an electrical voltage sensor, or the like or a combination thereof.

In one embodiment, the user-engageable element 114 may, for example, include a switch. When the user engages with the user-engageable element 114, the switch may be actuated to close an electric circuit and connect the sensor unit 104 to a power source (not shown) included, for example, as part of the drug delivery device 200. In one embodiment, the switch may, for example, include a single-use push-to-connect button. When the drug delivery device 200 is provided as a transdermal patch, the switch may be activated during the process of removing the patch from the user's skin. In such an embodiment, the user-engageable element 114 may be provided as a switch or a stress/strain gauge.

Figure 3:
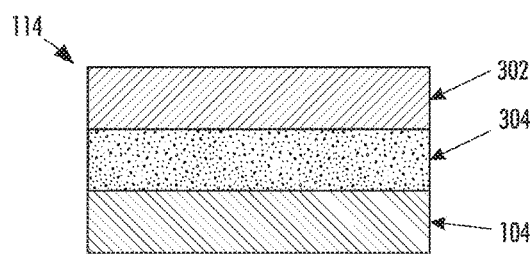
FIGS. 3-7 illustrate sensor unit according to some embodiments.

In another embodiment, and with reference to FIG. 3, the user-engageable element 114 may, for example, include an electrically conductive material 302 and a dielectric material 304 (e.g., air, a dielectric film, etc.) separating the electrically conductive material 302 from the sensor unit 104. The electrically conductive material 302 may be coupled to a power source (not shown) included, for example, as part of the drug delivery device 200 and may be considered a drive electrode. The electrode of the sensor unit 104 may be considered a sense electrode. When the user engages with the user-engageable element 114, the electrically conductive material 302 of the drive electrode and/or the dielectric material 304 may be deformed, thereby changing the capacitance between the electrically conductive material 302 and the dielectric material 304, which affects a voltage present at the sense electrode (i.e., the sensor unit 104).

Figure 4:
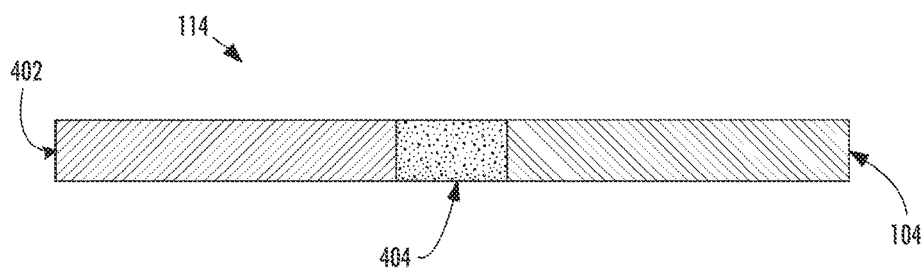

In yet another embodiment, and with reference to FIG. 4, the user-engageable element 114 may, for example, include an electrically conductive material 402 and a dielectric material 404 (e.g., air, a dielectric film, etc.) separating the electrically conductive material 402 from the sensor unit 104. The electrically conductive material 402 may be coupled to a power source (not shown) included, for example, as part of the drug delivery device 200 and may be considered a drive electrode. The electrode of the sensor unit 104 may be considered a sense electrode. When the user engages with the user-engageable element 114, a capacitance between the electrically conductive material 402 of the drive electrode and the sense electrode (i.e., the sensor unit 104) changes, which affects a voltage present at the sense electrode (i.e., the sensor unit 104).

In yet another embodiment, the user-engageable element 114 may, for example, include two electrodes of a normally open circuit, arranged at the surface of the drug delivery unit. The user may engage with the user-engageable element 114 by placing his or her finger or skin onto the two electrodes. When the user's finger or skin is placed onto the two electrodes, the normally open circuit is closed.

An optical characteristic of the user-engageable element 114 may, for example, include optical transmittance, index of refraction, optical reflectance, or the like or a combination thereof, which changes when the user engages with the user-engageable element 114. Accordingly, the sensor unit 104 may include at least one optical sensor such as a photodetector (e.g., sensitive to visible light, infra-red radiation, or the like) a light-emitting element (e.g., an LED) configured to illuminate the light photodetector (e.g., with visible light, infra-red radiation, or the like), or the like or a combination thereof.

In one embodiment, the user-engageable element 114 may, for example, include window through which light may be transmitted and an opaque layer covering the window, which may be removed by the user when the user engages with the user-engageable element 114. Therefore, the sensor unit 104 may include an optical sensor such as photodetector configured to detect light transmitted through the window.

In another embodiment, the user-engageable element 114 may, for example, include a light-emitting element (e.g., an LED) that may be activated to emit light when the user engages with the user-engageable element 114. Therefore, the sensor unit 104 may include an optical sensor such as photodetector configured to detect light emitted by the light-emitting element. The light-emitting element may, for example, emit visible light, infra-red light, or the like. In one embodiment, the light-emitting element emits a different wavelength of light corresponding to the drug retained within the drug-retaining region 102. In another embodiment, the light-emitting element emits pulses of light at different frequencies corresponding to the drug retained within the drug-retaining region 102.

A chemical characteristic of the user-engageable element 114 may, for example, include the chemical composition of a material adjacent to a sensor at a location within/adjacent to the user-engageable element 114, or the like, that changes when the user engages with the user-engageable element 114. Accordingly, the sensor unit 104 may include at least one chemical sensor such as a gas sensor (e.g., sensitive to air, carbon dioxide, carbon monoxide, oxygen, methane, or the like, or a combination thereof), a liquid sensor (e.g., sensitive to water, drug compositions, or the like, or a combination thereof), or the like or a combination thereof.

In one embodiment, the user-engageable element 114 may, for example, include a capsule containing a chemical. When the user engages with the user-engageable element 114, the capsule may be ruptured to release the chemical. Therefore, the sensor unit 104 may include a chemical sensor configured to detect the released chemical. In this embodiment, the chemical characteristic of the user-engageable element 114 may also be considered a mechanical characteristic.

In another embodiment, the user-engageable element 114 may, for example, include cavity adapted to receive a chemical. When the user engages with the user-engageable element 114, the user may provide a chemical (e.g., water, vinegar, or the like) within the cavity. Therefore, the sensor unit 104 may include a chemical sensor configured to detect the chemical provided within the cavity.

In another embodiment, the user-engageable element 114 may, for example, include a sensing interface of the sensor unit 104, wherein the sensor unit 104 is a pH sensor. When the user engages with the user-engageable element 114 (e.g., by placing a finger or skin onto the sensing interface of the sensor unit 104) the pH sensor may detect the user's skin.

In another embodiment, the user-engageable element 114 may include a seal covering the sensor unit 104. When the user engages with the user-engageable element 114 (e.g., by removing/breaking the seal), the sensor unit 104 is exposed to moisture, $CO_2$, air, etc.

When the sensor unit 104 includes at least one sensor arranged operably proximate to the user when the user is within an operable range of the drug delivery device 200 (e.g., at location III), the sensor unit 104 may detect a mechanical characteristic, a thermal characteristic, an electrical characteristic, an optical characteristic, a chemical characteristic, or the like or a combination thereof of the user that is dependent on the user being within an operable range of the drug delivery device 200 and generate an output corresponding to a value of the detected characteristic. Accordingly, the value of the characteristic detected by the sensor unit 104 may be outside a predetermined range when the user is outside the operable range of the drug delivery device 200. Therefore, the predetermined condition may be satisfied when the user is outside the operable range of the drug delivery device 200.

A mechanical characteristic of the user 110 may, for example, include the presence of the user's body within the operable range of the drug delivery device 200, the user's blood pressure, the user's heart rate, pore dilation of the user's skin, a force exerted by the user's body against the drug delivery device 200, or the like or a combination thereof, that can be detected when the user is within an operable range of the drug delivery device 200. Accordingly, the sensor unit 104 may include at least one sensor such as a proximity sensor (e.g., a capacitive-type, a magnetic-type, an inductive-type, an optical-type, an acoustic-type, or the like or a combination thereof), a blood pressure sensor, an optical sensor coupled with a light-emitting element, a pressure sensor, or the like or a combination thereof.

In one embodiment, the sensor unit 104 may be provided as exemplarily described above with respect to FIG. 3. In such an embodiment, one or more of the drive electrode, the dielectric material, and the sense electrode may be deformed by the user's body when the user is within the operable range of the drug delivery device 200. When one or more of the drive electrode, the dielectric material, and the sense electrode is deformed, the capacitance between the drive electrode and the sense electrode is changed, which affects a voltage present at the sense electrode. Implemented as exemplarily described herein, the sensor unit 104 is thus configured to detect a force exerted by the user's body. The voltage present at the sense electrode may constitute the output of the sensor unit 104.

In another embodiment, the sensor unit 104 may be provided as a piezoelectric element. When the user's body within the operable range of the drug delivery device 200, the piezoelectric element may be mechanically deformed. Upon being mechanically deformed, an electric current may be generated by the piezoelectric element as the output of the sensor unit 104. In one embodiment, the piezoelectric element may be mechanically deformed via direct contact with the user's body when the user's body is within the operable range of the drug delivery device 200. In another embodiment, sensor unit 104 may include an intermediate element that can be actuated by the user's body when the user's body is within the operable range of the drug delivery device 200. Upon being actuated, the intermediate element contacts the piezoelectric element.

A thermal characteristic of the user 110 may, for example, include temperature of the user, thermal conductivity of the user's tissue, thermal resistance of the user's tissue, or the like or a combination thereof, that can be detected when the user is within an operable range of the drug delivery device 200. Accordingly, the sensor unit 104 may include at least one temperature sensor such as a thermometer, a thermocouple, a temperature sensitive resistor, or the like or a combination thereof. In one embodiment, the sensor unit 104 may include a localized heater configured to control the temperature of a space adjacent to be within a specified range when the user's body is within the operable range of the drug delivery device 200 (e.g., due to a thermal resistance of the user's body). The thermometer (or thermocouple, or temperature sensitive resistor, etc.) may then sense a temperature decrease of the space when the user's body is outside the operable range of the drug delivery device 200.

An electrical characteristic of the user 110 may, for example, include a dielectric constant of the user's tissue, an electrical conductivity of the user's tissue, electrical inductance of the user's tissue, electrical impedance of the user's tissue, electrical resistance of the user's tissue, an electrical activity of the user's heart (ECG), or the like or a combination thereof, that can be detected when the user is within an operable range of the drug delivery device 200. Accordingly, the sensor unit 104 may include at least one electrical sensor such as an electrical resistance sensor, an electrical current sensor, an electrical voltage sensor, or the like or a combination thereof.

In one embodiment, the sensor unit 104 may be provided as exemplarily described above with respect to FIG. 4. In such an embodiment, the drive electrode and the sense electrode may be contacted by the user's body when the user is within the operable range of the drug delivery device 200. When the drive electrode and the sense electrode are contacted by the user's body, the capacitance between the drive electrode and the sense electrode is changed, which affects a voltage present at the sense electrode. Implemented as exemplarily described herein, the sensor unit 104 is thus configured to detect the dielectric constant of the user's tissue. The voltage present at the sense electrode may constitute the output of the sensor unit 104.

In another embodiment, the sensor unit 104 may include a drive electrode and a sense electrode similar to those described above with respect to FIG. 4, and may additionally include a seal electrically connecting the drive electrode and the sense electrode. The seal may be configured to be broken or removed from between the drive electrode and the sense electrode simultaneously with the removal of the user's body outside the operable range of the drug delivery device 200 (e.g., during the process of physically removing the drug delivery device 200 from the user's body). When the seal is broken or removed, the voltage present at the sense electrode changes, which constitutes the output of the sensor unit 104.

In another embodiment, the sensor unit 104 may include a first inductor coupled to the drug delivery device 200 and a second inductor coupled to the user's body. When the user's body is within an operable range of the drug delivery device 200, the first inductor is configured to be within a predetermined range of the second inductor and a predetermined coupling ratio is obtained between the inductors. However, when the user's body is outside the operable range of the drug delivery device 200, the first inductor is outside the predetermined range of the second inductor and the predetermined coupling ratio is not obtained. Thus, the output of the first inductor may constitute the output of the sensor unit 104.

Figure 5:
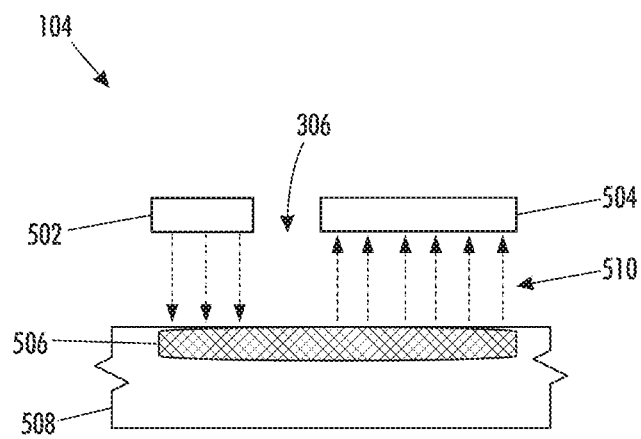

In another embodiment, and with reference to FIG. 5, the sensor unit 104 may include a driving electrode 502 and a sense electrode 504. The driving electrode 502 may be coupled to a power source (not shown) included, for example, as part of the drug delivery device 200. The drive electrode 502 and the sense electrode 504 may be spaced apart from the user's body by a predetermined distance or may contact the user's body when the user is within the operable range of the drug delivery device 200. When the drive electrode and the sense electrode are spaced apart from the user's body by the predetermined distance, the drive electrode 502 and the sense electrode 504 may be capacitively coupled to each other via an electrically differentiated region 506 (as shown by dashed arrows 510), which is coupled to the user's tissue 508 (e.g., skin). For purposes of discussion, the electrically differentiated region 506 may be considered as part of the user's tissue 508 in the sense that it is coupled thereto. When the drive electrode and the sense electrode contact the user's body, the drive electrode 502 and the sense electrode 504 may be conductively coupled to each other via the electrically differentiated region 506. Implemented as exemplarily described herein, the sensor unit 104 is thus configured to detect the electrical conductivity of the user's tissue. The voltage present at the sense electrode may constitute the output of the sensor unit 104 and, therefore, corresponds to the electrical conductivity of the user's tissue.

The electrically differentiated region 506 may contain a material having an electrical conductivity that is different from the user has a higher electrical conductivity than the user's tissue 508. For example, the electrically differentiated region 506 may contain a material having an electrical conductivity that is greater than that of the user's tissue 508. In the illustrated embodiment, the electrically differentiated region 506 is disposed within the user's tissue 508 and may be provided as an electrically-conductive ink that is injectable into the user's skin, an electrically-conductive plate inserted into the user's skin, or the like or a combination thereof. The electrically-conductive ink may, for example, include a metal that is biocompatible (i.e., inert within the user's tissue 508) such as gold, titanium, platinum, palladium, or the like or a combination thereof. In another example, the electrically-conductive ink may include a metal that is not biocompatible (e.g., silver, nickel, tungsten, or the like or a combination thereof) that is coated with a biocompatible material such as silicone, Teflon®, parylene C, or the like or a combination thereof. In another embodiment, the electrically differentiated region 506 is disposed on the user's tissue 508 and may be provided an electrically-conductive film adhered to the user's tissue 508 (e.g., as a sticker). In the illustrated embodiment, the electrically differentiated region 506 extends contiguously under substantially the entire area of at least one of the driving electrode 502 and the sense electrode 504.

As described above with respect to FIG. 5, the driving electrode 502 and may be capacitively coupled to the sense electrode 504 via the electrically differentiated region 506 when the user is within the operable range of the drug delivery device 200. Thus, the value of the signal output by the sensor unit 104 corresponds to the size of the overlapping area between the driving electrode 502 and the electrically differentiated region 506 in addition to the size of the overlapping area between the sense electrode 504 and the electrically differentiated region 506. In one embodiment, the value of the voltage obtained at the sense electrode 504 is within a predetermined range when the drug delivery device 200 is arranged such that the drive electrode 502 and/or the sense electrode 504 overlaps the electrically differentiated region 506, or such that the drive electrode 502 and/or the sense electrode 504 overlap a sufficient area of the electrically differentiated region 506. Accordingly, the value of the voltage obtained at the sense electrode 504 is outside a predetermined range when the drug delivery device 200 is arranged such that the drive electrode 502 and/or the sense electrode 504 does not overlap the electrically differentiated region 506, or such that the drive electrode 502 and/or the sense electrode 504 do not overlap a sufficient area of the electrically differentiated region 506. Therefore, when the value of the voltage obtained at the sense electrode 504 is outside a predetermined range, the user is considered to be outside the operable range of the drug delivery device 200.

Figure 6:
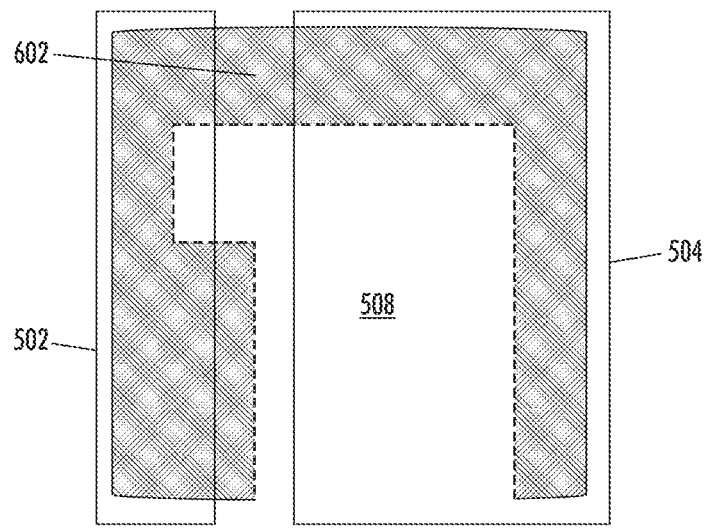

As exemplarily illustrated in FIG. 5, the electrically differentiated region 506 is provided under substantially the entire area of at least one of the driving electrode 502 and the sense electrode 504. According to another embodiment, and with reference to FIG. 6, the aforementioned electrically differentiated region 506 may be replaced with an electrically differentiated region 602, provided in substantially the same manner as the electrically differentiated region 506, extending contiguously under the driving electrode 502 and the sense electrode 504; but extending under only a portion of the entire area of the driving electrode 502, under only a portion of the entire area of the sense electrode 504, or a combination thereof. What constitutes a "sufficient area" of overlap between the drive electrode 502 and/or the sense electrode 504 with the electrically differentiated region 602 may be determined by a third party (e.g., a physician prescribing the drug contained within the drug-retaining region 102, a pharmacist providing the drug delivery device 200, or the like). In this manner, only the intended user of the drug contained within drug-retaining region 102 will be capable obtaining the drug through proper use of the drug delivery device 200.

Figure 7:
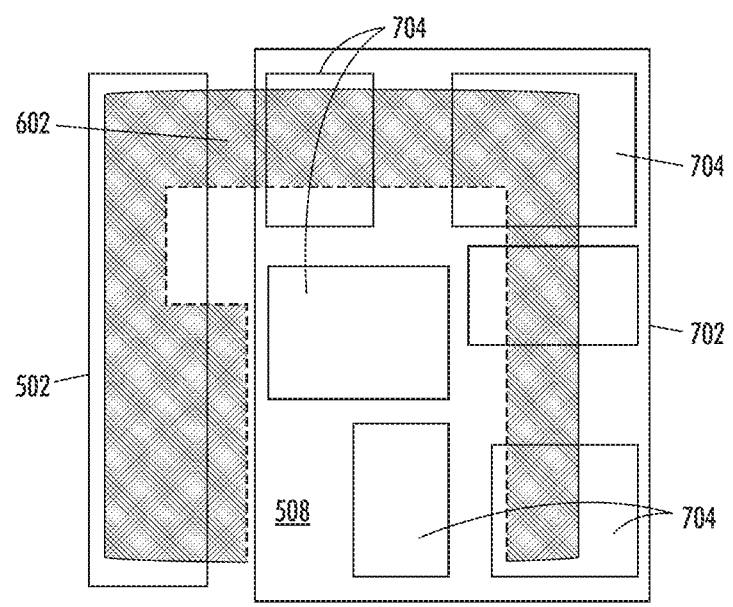

According to another embodiment, and with reference to FIG. 7, the aforementioned sense electrode 504 may be replaced with an array 702 of a plurality of sense electrodes 704 having different areas, which are electrically connected to each other. At least one of the plurality of sense electrodes 704 may overlap the electrically differentiated region 602 and at least one of the plurality of sense electrodes 704 may not overlap the electrically differentiated region 602. Although not illustrated, the aforementioned driving electrode 502 may additionally, or alternatively, be replaced with an array of a plurality of driving electrodes having different areas, which are electrically connected to each other such that at least one of the plurality of driving electrodes overlaps the electrically differentiated region 602 and at least one of the plurality of driving electrodes does not overlap the electrically differentiated region 602.

In one embodiment, the value of the collective voltage obtained at the plurality of sense electrodes 704 is within a predetermined range when the drug delivery device 200 is arranged such that predetermined ones of the plurality of sense electrodes 704 within the array of sense electrodes 702 overlap the electrically differentiated region 602, or such that predetermined ones of the plurality of sense electrodes 704 within the array of sense electrodes 702 overlap a sufficient area of the electrically differentiated region 602. Accordingly, the value of the collective voltage obtained at the plurality of sense electrodes 704 is outside a predetermined range when the drug delivery device 200 is arranged such that predetermined ones of the plurality of sense electrodes 704 within the array of sense electrodes 702 do not overlap the electrically differentiated region 602, or such that predetermined ones of the plurality of sense electrodes 704 within the array of sense electrodes 702 do not overlap a sufficient area of the electrically differentiated region 602.

Similar to the embodiment discussed above with respect to FIG. 6, what constitutes a "sufficient area" of overlap between the plurality of sense electrodes 704 within the array of sense electrodes 702 with the electrically differentiated region 602 may be determined by a third party (e.g., a physician prescribing the drug contained within the drug-retaining region 102, a pharmacist providing the drug delivery device 200, or the like). In this manner, only the intended user of the drug contained within drug-retaining region 102 will be capable obtaining the drug through proper use of the drug delivery device 200. In another embodiment, the predetermined ones of the plurality of sense electrodes 704 within the array of sense electrodes 702 may be identified by a third party such as the manufacturer of the drug delivery device 200, the physician prescribing the drug contained within the drug-retaining region 102, the pharmacist providing the drug delivery device 200, or the like. In this manner, only the intended user of the drug contained within drug-retaining region 102 will be capable obtaining the drug through proper use of the drug delivery device 200.

As exemplarily described above, the sensor unit 104 may be configured to detect the electrical conductivity of the user's tissue (i.e., the electrically differentiated region 506). In other embodiments, however, the sensor unit 104 may be configured to detect a magnetic characteristic or a dielectric constant of the user's tissue.

For example, the electrically differentiated region 506 may be replaced with a magnetically differentiated region containing a material having a detectable magnetic property (e.g., a ferromagnetic material such as iron oxide, cobalt, magnesium oxide, or the like or a combination thereof). A current flow can be induced within the magnetically differentiated region when the user's body is removed to be outside the operable range of the drug delivery device 200.

In another example, the electrically differentiated region 506 may be replaced with a dielectrically differentiated region containing a material (e.g., silicon oxide, silicon oxynitride, or the like or a combination thereof) having a relatively large dielectric constant compared to that of the user's tissue.

An optical characteristic of the user 110 may, for example, include optical transmittance of the user's tissue, index of refraction of the user's tissue, optical reflectance of the user's tissue, spectral emission of the user's tissue, or the like or a combination thereof that can be detected when the user is within an operable range of the drug delivery device 200. Accordingly, the sensor unit 104 may include at least one optical sensor such as a photodetector (e.g., sensitive to visible light, infra-red radiation, or the like) a light-emitting element (e.g., an LED) configured to illuminate the light photodetector (e.g., with visible light, infra-red radiation, or the like), or the like or a combination thereof.

In one embodiment, the sensor unit 104 may include at least one optical sensor such as a photodetector (e.g., sensitive to visible light, infra-red light, ultraviolet light, or the like) and a seal configured to optically shield the at least one photodetector. The seal may be configured to be broken or removed from the at least one photodetector simultaneously with the removal of the user's body outside the operable range of the drug delivery device 200 (e.g., during the process of physically removing the drug delivery device 200 from the user's body). When the seal is broken or removed, the photodetector detects the increased intensity of light, which constitutes the output of the sensor unit 104.

In another embodiment, the sensor unit 104 may be provided in a similar manner as discussed above with respect to FIGS. 5-7, but the driving electrode 502 may be replaced by one or more light-emitting elements, the sense electrode 504 (or 704) may be replaced by one or more photodetectors, and the electrically differentiated region 506

(or 602) may be replaced by an optically differentiated region coupled to the user's tissue 508.

In one embodiment, the optically differentiated region may contain a material having an optical characteristic that is different from an optical characteristic of the user's tissue 508. For example, the material may absorb, transmit, refract light emitted by the one or more light-emitting elements differently from the user's tissue 508. In one embodiment, the material of the optically differentiated region may fluoresce in the presence of light emitted by the one or more light-emitting elements.

In one embodiment, the optically differentiated region may be disposed within the user's tissue 508 and may be provided as an ink that is injectable into the user's skin, a plate inserted into the user's skin, or the like or a combination thereof. In another embodiment, the optically differentiated region is disposed on the user's tissue 508 and may be provided as a film adhered to the user's tissue 508 (e.g., as a sticker).

In one embodiment, the optically differentiated region may be provided as one or more light-emitting element disposed on the user's tissue 508 (e.g., by the use of an adhesive, a strap formed around a part of the user's body, etc.). In such an embodiment, the sensor unit 104 includes one or more photodetectors configured to receive light emitted by the one or more light-emitting elements when the user is within an operable range of the drug delivery device 200.

A chemical characteristic of the user 110 may, for example, include the presence of the user's perspiration, ion concentration in the user's perspiration, pH of the user's perspiration, chemical composition of the user's tissue, or the like or a combination thereof that can be detected when the user is within an operable range of the drug delivery device 200. Accordingly, the sensor unit 104 may include at least one chemical sensor such as a moisture sensor, a pH sensor, or the like, or a combination thereof) or the like or a combination thereof.

When the sensor unit 104 includes at least one sensor arranged operably proximate to the external environment 112 (e.g., at location IV), the sensor unit 104 may detect a mechanical characteristic, a thermal characteristic, an electrical characteristic, an optical characteristic, a chemical characteristic, or the like or a combination thereof of the external environment 112 and generate an output corresponding to a value of the detected characteristic. Accordingly, the value of the characteristic detected by the sensor unit 104 may be outside a predetermined range when the external environment 112 is not the predetermined environment of the drug delivery device 200. Therefore, the predetermined condition may be satisfied when the external environment 112 is not the predetermined environment of the drug delivery device 200.

A mechanical characteristic of the external environment 112 may, for example, include pressure, or the like. Accordingly, the sensor unit 104 may include at least one sensor such as a pressure sensor or the like or a combination thereof. In another example, a mechanical characteristic of the external environment 112 may include acoustic wave propagation of the external environment 112. Accordingly, the sensor unit 104 may include an acoustic emitter (e.g., a speaker) and an acoustic detector (e.g., a microphone), wherein the acoustic detector may monitor a change in propagation velocity of acoustic waves emitted by the acoustic emitter, phase change, the transmitted intensity, reflected intensity, scattered intensity, absorbed intensity, or the like or a combination thereof.

A thermal characteristic of the external environment 112 may, for example, include temperature, or the like. Accordingly, the sensor unit 104 may include at least one temperature sensor such as a thermometer, a thermocouple, a temperature sensitive resistor, or the like or a combination thereof.

An electrical characteristic of the external environment 112 may, for example, include dielectric constant, electrical conductivity, electrical inductance, electrical impedance, electrical resistance, or the like or a combination thereof. Accordingly, the sensor unit 104 may include at least one electrical sensor such as an electrical resistance sensor, an electrical current sensor, an electrical voltage sensor, or the like or a combination thereof.

An optical characteristic of the external environment 112 may, for example, include brightness. Accordingly, the sensor unit 104 may include at least one optical sensor such as a photodetector (e.g., sensitive to visible light, infra-red light, ultraviolet light, or the like). Accordingly, the sensor unit 104 may include at least one optical sensor such as a photodetector (e.g., sensitive to visible light, infra-red light, ultraviolet light, or the like) configured to detect an optical characteristic of the external environment 112. In one example, the sensor unit 104 may further include a light-emitting element (e.g., an LED) configured to transmit light (e.g., visible light, infra-red light, ultraviolet light or the like) through the external environment 112.

A chemical characteristic of the external environment 112 may, for example, include the presence of a chemical such as water (e.g., present in liquid or vapor form), or the like. Accordingly, the sensor unit 104 may include at least one chemical sensor such as a gas sensor (e.g., sensitive to air, carbon dioxide, carbon monoxide, oxygen, methane, or the like, or a combination thereof), a liquid sensor (e.g., sensitive to water, drug compositions, or the like, or a combination thereof), a pH sensor, or the like or a combination thereof.

Figure 8:
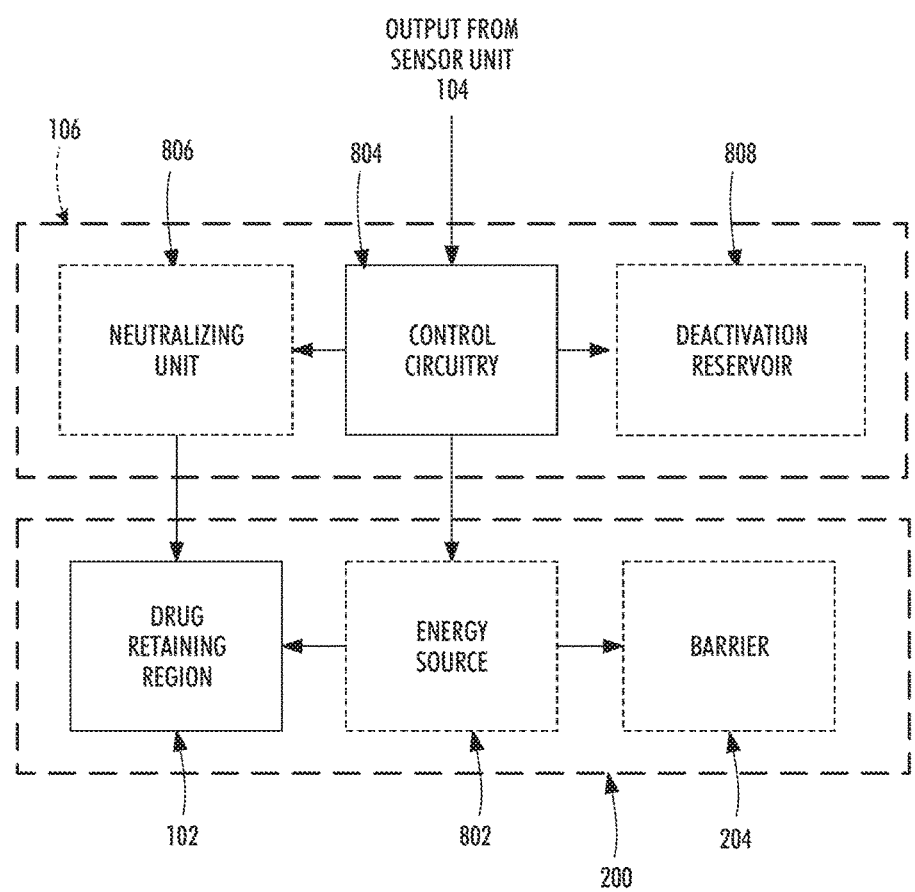
FIG. 8 schematically illustrates elements of the deactivation unit shown in FIG. 1, according to some embodiments.

FIG. 8 schematically illustrates elements of the deactivation unit shown in FIG. 1, according to some embodiments.

As mentioned above, a drug may be rendered "ineffective" when the drug cannot be cannot be transported from the drug-retaining region 102 to a location outside the drug delivery device.

Accordingly, in one embodiment, the drug cannot be removed from the drug-retaining region 102 when the drug is prevented from being diffused through the barrier 204 of the drug delivery device 200. Accordingly, and with reference to FIG. 8, the drug delivery device 200 may include an energy source 802 configured to supply energy to the drug-retaining region 102, the barrier 204 or a combination thereof. Energy supplied by the energy source 802 may be used to facilitate transport of the drug from the drug-retaining region 102 to a location outside the drug delivery device 200 (e.g., to the user's tissue). Energy supplied by the energy source 802 may be ultrasonic vibrations, an electrical field, or the like or a combination thereof. As also shown in FIG. 8, the deactivation unit 106 may, for example, include control circuitry 804 configured to prevent the energy from being supplied from the energy source 802. As used herein, the term "circuitry" refers to any type of executable instructions that can be implemented as, for example, hardware, firmware, and/or software. Thus, the control circuitry 804 may be provided as a dedicated fixed-purpose circuit and/or one or more partially or wholly programmable circuits.

In one embodiment, the drug may be rendered "ineffective" by preventing the drug from being transported from the drug-retaining region 102 to a location outside the drug delivery device, in the manner exemplarily described above, when an output of the sensor unit 104 having at least one sensor at one or more of locations I-IV described above with respect to FIG. 2 satisfies a predetermined condition.

As mentioned above, a drug may be rendered "ineffective" when the drug is neutralized within the drug-retaining region 102.

Accordingly, in one embodiment, the deactivation unit 106 may include a neutralizing unit 806 coupled to the control circuitry 804. The neutralizing unit 806 may be configured to neutralize the drug within the drug-retaining region 102. The neutralizing unit 806 may be disposed outside the drug-retaining region 102, within the drug-retaining region 102, or a combination thereof.

In one embodiment, the neutralizing unit 806 is configured to neutralize the drug within the drug-retaining region 102 by supplying energy (e.g., electricity, light, heat, or the like) to the drug within the drug-retaining region 102. In another embodiment, the neutralizing unit 806 may include capsules exposed to the drug-retaining region 102. The capsules may contain a material and be degradable by any suitable means to release the material within the drug-retaining region 102. When the material is released within the drug-retaining region 102, the drug is rendered ineffective. Examples of the neutralizing unit 806 can be found in co-pending U.S. patent application Ser. No. 12/357,108 entitled "DRUG DEACTIVATION SYSTEM AND METHOD OF DEACTIVATING A DRUG USING THE SAME," the disclosure of which is incorporated herein by reference in its entirety.

In one embodiment, the drug may be rendered "ineffective" by neutralizing the drug within the drug-retaining region 102, in the manner exemplarily described above, when an output of the sensor unit 104 having at least one sensor at one or more of locations I-IV described above with respect to FIG. 2 satisfies a predetermined condition.

As mentioned above, a drug may be rendered "ineffective" when the bio-activity of the drug is blocked within the user.

Accordingly, in one embodiment, the deactivation unit 106 may, for example, include a deactivation reservoir 808 coupled to the control circuitry 804. The deactivation reservoir 808 may contain a substance configured to render the drug ineffective within the user. In one embodiment, the substance may be transported from the deactivation reservoir 808 to the user in the same manner or in a different manner as the drug is transported from the drug-retaining region 102 to the user. In one embodiment, the substance contained within the deactivation reservoir 808 may include an antagonist to the drug within the drug-retaining region 102. Nevertheless, it will be appreciated that the substance contained within the deactivation reservoir 808 may include any suitable substance based on the drug retained within the drug-retaining region 102. Table 1 identifies some examples of substances that may be contained within the deactivation reservoir 808, depending on some exemplary drugs that may be retained within the drug-retaining region 102.

TABLE 1

| Medical Application | Drug retained within drug-retaining region 102 | Substance contained within deactivation reservoir 808 |
|---|---|---|
| Pain management | morphine, codeine, hydromorphone, hydrocodone, oxycodone, oxymorphone, desomorphine, diacetylmorphine, nicomorphine, dipropanoylmorphie, benzylmorphine, pethidine, methadone, tramadol, propoxyphene, endorphins, enkephalins, dynorphins, endomorphins. | Cyprodime, Naltrindole, Norbinaltorphimine, Hydrogen peroxide, metabolizing enzymes such as NADH and NADPH, caustic reactants, such as NAOH, KOH, trimethylamine |
| Antibiotics | Penicillin, cephalosporins, other β-lactam antibiotics, Aminoglycosidic antibiotics fluoroquinolones, nitrofurans, vancomycin, monobactams, co-trimoxazole, metronidazole | β-lactamase enzyme, strong acids, strong bases |
| anti-convulsants | Aldehydes, Aromatic allylic alcohols, Barbiturates, Benzodiazepines, Bromides, Carbamates, Carboxamides, Fatty acids, Fructose derivatives, Gaba analogs, Hydantoins, Oxazolidinediones, Propionates, Pyrimidinediones, Pyrrolidines, Succinimides, Sulfonamides, Triazines, Ureas, Valproylamides | Strong acids, strong bases |
| Reproductive Hormones | Amine-derived hormones: catecholamines, thyroxine; Peptide hormones: TRH, vasopressin; Protein hormones: insulin, growth hormone, luteinizing hormone, follicle-stimulating hormone, thyroid-stimulating hormone; testosterone, cortisol, calcitriol | Strong acids, strong bases, hydrolytic enzymes |

In one embodiment, the bio-activity of the drug contained within the drug-retaining region 102 may be blocked within the user, in the manner exemplarily described above, when an output of the sensor unit 104 having at least one sensor at one or more of locations I-IV described above with respect to FIG. 2 satisfies a predetermined condition.

In another embodiment, the sensor unit 104 is configured to detect a physiological characteristic of the user and the predetermined condition is satisfied when the physiological characteristic detected by the sensor unit 104 indicates that the user has overdosed on the drug within the drug-retaining region 102.

For example, when the sensor unit 104 is operatively coupled to the user's tissue in the manner as described with respect to FIG. 2, and the user is not overdosing on the drug within the drug-retaining region 102, a detected physiological characteristic of the user is within a representative range. However, when the user is overdosing on the drug within the drug-retaining region 102, the detected physiological characteristic of the user is outside the representative range. When the detected physiological characteristic of the user is outside the representative range, a characteristic of the signal output by the sensor unit 104 indicates that the user is overdosing. Accordingly, the output signal of the sensor unit 104 indicates that the predetermined condition is satisfied. Upon receipt of the output signal of the sensor unit 104, the deactivation unit 106 is actuated to render the drug contained within the drug-retaining region 102 ineffective.

It will be appreciated that several of the above-disclosed and other features and functions, or alternatives thereof, may be desirably combined into many other different systems or applications. It will also be appreciated that various presently unforeseen or unanticipated alternatives, modifications, variations, or improvements therein may be subsequently made by those skilled in the art which are also intended to be encompassed by the following claims.

What is claimed is:

1. A system for use with a drug delivery device having a drug in a reservoir, the system comprising:
    a sensor unit configured to detect a characteristic in a local environment and generate an output corresponding to a value of the detected characteristic; and
    a deactivation unit operatively coupled to the sensor unit and to the reservoir, the deactivation unit having control circuitry and an energy source, the control circuitry configured to initiate application of energy from the energy source to the reservoir;
    wherein the control circuitry is configured to apply the energy to the reservoir to neutralize the drug in the reservoir when the sensor unit detects a condition in the local environment using the characteristic of the local environment.

2. The system of claim 1, wherein the sensor unit configured to detect a condition in the local environment detects a characteristic of a user.

3. The system of claim 2, wherein the sensor unit configured to detect a condition in the local environment further comprises a user engageable element coupled to the drug delivery device.

4. The system of claim 1, wherein the sensor unit configured to detect a condition in the local environment further comprises at least one characteristic in the local environment selected from the group consisting of a mechanical characteristic, a thermal characteristic, an electrical characteristic, an optical characteristic and a chemical characteristic.

5. The system of claim 1, wherein the condition is satisfied when the value of the detected characteristic in the local environment is outside a predetermined range.

6. The system of claim 1, wherein the condition is satisfied when the value of the detected characteristic in the local environment is within a predetermined range.

7. The system of claim 1, wherein the condition is satisfied when a rate at which the value of the detected characteristic in the local environment changes is outside a predetermined range.

8. The system of claim 1, wherein the condition is satisfied when a user engages with a user engageable element coupled to the drug delivery device.

9. The system of claim 1, wherein the drug is transportable from the reservoir to a user upon application of energy from the energy source to the reservoir.

10. The drug delivery device of claim 9, wherein the deactivation unit is further configured to discontinue the application of energy from the energy source to the reservoir when the output of the sensor unit satisfies the condition.

11. A system for use with a drug delivery device having a drug in a reservoir, the system comprising:
    a sensor unit configured to detect a characteristic in a local environment and generate an output corresponding to a value of the detected characteristic; and
    a deactivation unit operatively coupled to the sensor unit and to the reservoir, the deactivation unit having control circuitry and a capsule, the control circuitry configured to expose the capsule to the reservoir;
    wherein the control circuitry is configured to expose the capsule to the reservoir to neutralize the drug when the sensor unit detects a condition in the local environment using the characteristic of the local environment.

12. The system of claim 11, wherein the drug delivery device includes at least one selected from the group consisting of an inhaler, a syringe, an intravenous bag, an implanted drug delivery system, a transdermal patch, a pill bottle, a liquid medicine bottle and an eyedropper.

13. The system of claim 11, further comprising a housing, wherein the reservoir is located within the housing, and wherein the sensor unit comprises at least one sensor coupled to the housing.

14. The system of claim 11, wherein the capsule is degradable and contains material to neutralize the drug in the reservoir when the condition is satisfied.

15. The system of claim 11, further comprising a user engageable element that is detectable by the sensor unit when a user engages with the user engageable element.

16. A method for using of a drug delivery device having a reservoir operatively coupled to a deactivation unit and a sensor unit, the reservoir containing a drug, the deactivation unit having control circuitry and an energy source, the method comprising:
    detecting, using the sensor unit, a characteristic in a local environment;
    outputting, at the sensor unit, a signal corresponding to the detected characteristic;
    receiving the output value of the signal corresponding to the detected characteristic at the control circuitry; and
    responsive to receiving the output value at the control circuitry, outputting a signal from the control circuitry to the energy source and applying energy from the energy source to the reservoir to neutralize the drug when the sensor unit outputs a signal indicating detection of a condition in the local environment using the characteristic in the local environment.

17. The method of claim 16, wherein said outputting outputs the signal when the value of the detected characteristic in the local environment is outside a predetermined range.

18. The method of claim 16, wherein said outputting outputs the signal when the value of the detected characteristic in the local environment is within a predetermined range.

19. The method of claim 16, wherein said detecting detects at least one characteristic in a local environment selected from the group consisting of a mechanical characteristic, a thermal characteristic, an electrical characteristic, an optical characteristic and a chemical characteristic.

20. A method of use of a drug delivery device having a reservoir operatively coupled to a deactivation unit and a sensor unit, the reservoir containing a drug, the deactivation unit having control circuitry and a capsule, the control circuitry configured to expose the capsule to the reservoir, the method comprising:
    detecting, using the sensor unit, a characteristic in a local environment;
    outputting, at the sensor unit, an output value corresponding to the detected characteristic;
    receiving the output value at the control circuitry; and
    responsive to receiving the output value corresponding to the detected characteristic at the control circuitry, outputting a signal from the control circuitry to the energy source and exposing the capsule to the reservoir to neutralize a drug in the reservoir when the sensor unit outputs an output value indicating the detection of a condition in the local environment using the characteristic of the local environment.

21. The method of claim 20, wherein said outputting outputs the output value when the output value of the detected characteristic in the local environment is outside a predetermined range.

22. The method of claim 20, wherein said outputting outputs the output value when the output value of the detected characteristic in the local environment is within a predetermined range.

23. The method of claim 20, wherein said detecting detects at least one characteristic in a local environment selected from the group consisting of a mechanical characteristic, a thermal characteristic, an electrical characteristic, an optical characteristic and a chemical characteristic.

* * * * *